US005120461A

United States Patent [19]

Logsdon et al.

[11] Patent Number: 5,120,461

[45] Date of Patent: Jun. 9, 1992

[54] AZEOTROPE-LIKE COMPOSITIONS OF 1,1-DICHLORO-1-FLUOROETHANE; DICHLOROTRIFLUOROETHANE; METHANOL; AND ALKENE HAVING 5 CARBON ATOMS

[75] Inventors: Peter B. Logsdon, North Tonawanda; Ellen L. Swan, Ransomville; Leonard M. Stachura, Hamburg; Rajat S. Basu, Williamsville, all of N.Y.

[73] Assignee: Allied-Signal Inc., Morris Township, Morris County, N.J.

[21] Appl. No.: 570,576

[22] Filed: Aug. 21, 1990

[51] Int. Cl.[5] .......................... C11D 7/30; C11D 7/50; C23G 5/028; C07C 17/42

[52] U.S. Cl. .......................... 252/171; 134/12; 134/31; 134/38; 134/39; 134/40; 252/162; 252/170; 252/364; 252/DIG. 9; 570/121; 570/122

[58] Field of Search ............... 252/162, 170, 171, 364, 252/DIG. 9; 134/12, 31, 38, 39, 40; 570/121, 122

[56] References Cited

U.S. PATENT DOCUMENTS

| | | | |
|---|---|---|---|
| 4,836,947 | 6/1989 | Lund et al. | 252/171 |
| 4,842,764 | 6/1989 | Lund et al. | 252/171 |
| 4,863,630 | 9/1989 | Swan et al. | 252/171 |
| 4,894,175 | 1/1990 | Swan et al. | 252/171 |
| 4,994,201 | 2/1991 | Stachura et al. | 252/171 |
| 4,996,242 | 2/1991 | Lin | 521/131 |

FOREIGN PATENT DOCUMENTS

| | | |
|---|---|---|
| 01-139539 | 6/1987 | Japan . |
| 103686 | 4/1989 | Japan . |
| 1-132539 | 5/1989 | Japan . |
| 136981 | 5/1989 | Japan . |
| 136982 | 5/1989 | Japan . |
| 137253 | 5/1989 | Japan . |
| 137259 | 5/1989 | Japan . |
| 138300 | 5/1989 | Japan . |
| 139104 | 5/1989 | Japan . |
| 1-139540 | 6/1989 | Japan . |
| 139861 | 6/1989 | Japan . |
| 90/08814 | 8/1990 | PCT Int'l Appl. . |

OTHER PUBLICATIONS

*CRC Handbook of Chemistry and Physics*, ed. R. Weast, CRC Press Florida, 63rd Edition (1982–1983) pp. C–194 and C–421.

*Primary Examiner*—A. Lionel Clingman
*Assistant Examiner*—Linda Skaling
*Attorney, Agent, or Firm*—Melanie L. Brown; Jay P. Friedenson

[57] ABSTRACT

Azeotrope-like compositions comprising 1,1-dichloro-1-fluoroethane; dichlorotrifluoroethane; methanol; and alkene having 5 carbon atoms are stable and have utility as degreasing agents and as solvents in a variety of industrial cleaning applications including cold cleaning and defluxing of printed circuit boards and dry cleaning.

9 Claims, No Drawings

AZEOTROPE-LIKE COMPOSITIONS OF 1,1-DICHLORO-1-FLUOROETHANE; DICHLOROTRIFLUOROETHANE; METHANOL; AND ALKENE HAVING 5 CARBON ATOMS

FIELD OF THE INVENTION

This invention relates to azeotrope-like mixtures of 1,1-dichloro-1-fluoroethane; dichlorotrifluoroethane; methanol; and alkene having 5 carbon atoms. These mixtures are useful in a variety of vapor degreasing, cold cleaning and solvent cleaning applications including defluxing and dry cleaning.

CROSS-REFERENCE TO RELATED APPLICATIONS

Co-pending, commonly assigned patent application Ser. No. 345,732, filed May 1, 1989, now abandoned discloses azeotrope-like mixtures of 1,1-dichloro-1-fluoroethane; dichlorotrifluoroathane; nitromethane; and methanol or ethanol.

Co-pending, commonly assigned patent application Ser. No. 412,080, filed Sep. 25, 1989, now U.S. Pat. No. 4,994,201 discloses azeotrope-like compositions of 1,1-dichloro-1-fluoroethane; dichlorotrifluoroethane; methanol; and cyclopentane.

Co-pending, commonly assigned patent application Ser. No. 417,134, filed Oct. 4, 1989, now U.S. Pat. No. 4,965,011 discloses azeotrope-like mixtures of 1,1-dichloro-1-fluoroethane; dichlorotrifluoroethane; and nitromethane.

Co-pending, commonly assigned patent application Ser. No. 423,993, filed Oct. 19, 1989, now abandoned discloses azeotrope-like compositions of dichlorotrifluoroethane and methanol.

Co-pending, commonly assigned patent application Serial No. 435,842, filed Nov. 10, 1989, now U.S. Pat. No. 4,960,535 discloses azeotrope-like compositions of 1,1-dichloro-1-fluoroethane; dichlorotrifluoroethane; and a mono- or di-chlorinated $C_2$ or $C_3$ alkane.

Co-pending, commonly assigned patent application Ser. No. 435,923, filed Nov. 10, 1989, now U.S. Pat. No. 5,024,781 discloses azeotrope-like compositions of 1,1-dichloro-1-fluoroethane; dichlorotrifluoroethane; methanol; and a mono- or di-chlorinated $C_2$ or $C_3$ alkane.

Co-pending, commonly assigned patent application Ser. No. 439,752, filed Nov. 21, 1989, which is a continuation-in-part of Ser. No. 362,294, filed Jun. 6, 1989, discloses azeotrope-like compositions of 1,1-dichloro-1-fluoroethane and dichlorotrifluoroethane.

Co-pending, commonly assigned patent application Ser. No. 451,076, filed Dec. 15, 1989, now abandoned discloses azeotrope-like compositions of 1,1-dichloro-1-fluoroethane; 1,1-dichloro-2,2,2-trifluoroethane; 1,2-dichloro-1,1,2-trifluoroethane; and methanol.

Co-pending, commonly assigned patent application Ser. No. 453,449, filed Dec. 20, 1989, now U.S. Pat. No. 5,049,301 discloses azeotrope-like compositions of 1,1-dichloro-1-fluoroethane; dichlorotrifluoroethane; and methyl formate.

Co-pending, commonly assigned patent application Ser. No. 455,709, filed Dec. 22, 1989, now U.S. Pat. No. 5,026,501 discloses azeotrope-like compositions of 1,1-dichloro-1-fluoroethane; dichlorotrifluoroethane; and dichloromethane.

BACKGROUND OF THE INVENTION

Vapor degreasing and solvent cleaning with fluorocarbon based solvents have found widespread use in industry for the degreasing and otherwise cleaning of solid surfaces, especially intricate parts and difficult to remove soils.

In its simplest form, vapor degreasing or solvent cleaning consists of exposing a room temperature object to be cleaned to the vapors of a boiling solvent. Vapors Condensing on the object provide clean distilled solvent to wash away grease or other contamination. Final evaporation of solvent from the object leaves behind no residue as would be the case where the object is simply washed in liquid solvent.

For difficult to remove soils where elevated temperature is necessary to improve the cleaning action of the solvent, or for large volume assembly line operations where the cleaning of metal parts and assemblies must be done efficiently and quickly, the conventional operation of a vapor degreaser consists of immersing the part to be cleaned in a sump of boiling solvent which removes the bulk of the soil, thereafter immersing the part in a sump containing freshly distilled solvent near room temperature, and finally exposing the part to solvent vapors over the boiling sump which condense on the cleaned part. In addition, the part can also be sprayed with distilled solvent before final rinsing.

Vapor degreasers suitable in the above-described operations are well known in the art. For example, Sherliker et al. in U.S. Pat. No. 3,085,918 disclose such clean sump, a water separator, and other ancillary equipment.

Cold clearing is another application where a number of solvents are used. In most cold cleaning applications, the soiled part is either immersed in the fluid or wiped with rags or similar objects soaked in solvents and allowed to air dry.

Fluorocarbon solvents, such as trichlorotrifluoroethane, have attained widespread use in recent years as effective, nontoxic, and nonflammable agents useful in degreasing applications and other solvent cleaning applications. Trichlorotrifluoroethane has been found to have satisfactory solvent power for greases, oils, waxes and the like. It has therefore found widespread use for cleaning electric motors, compressors, heavy metal parts, delicate precision metal parts, printed circuit boards, gyroscopes, guidance systems, aerospace and missile hardware, aluminum parts and the like.

The art has looked towards azeotrope or azeotrope-like compositions including the desired fluorocarbon components such as trichlorotrifluoroethane which include components which contribute additionally desired characteristics, such as polar functionality, increased solvency power, and stabilizers. Azeotropic or azeotrope-like compositions are desired because they do not fractionate upon boiling. This behavior is desirable because in the previously described vapor degreasing equipment with which these solvents are employed, redistilled material is generated for final rinse-cleaning. Thus, the vapor degreasing system acts as a still. Unless the solvent composition exhibits a constant boiling point, i.e., is azeotrope-like, fractionation will occur and undesirable solvent distribution may act to upset the cleaning and safety of processing. Preferential evaporation of the more volatile components of the solvent mixtures, which would be the case if they were not azeotrope-like, would result in mixtures with changed compositions which may have less desirable properties, such as lower solvency towards soils, less inertness towards metal, plastic or elastomer components, and increased flammability and toxicity.

The art is continually seeking new fluorocarbon based azeotrope-like mixtures which offer alternatives for new and special applications for vapor degreasing and other cleaning applications. Currently, of particular interest, are fluorocarbon based azeotrope-like mixtures which are considered to be stratospherically safe substitutes for presently used fully halogenated chlorofluorocarbons. The latter are suspected of causing environmental problems in connection with the earth's protective ozone layer. Mathematical models have substantiated that hydrochlorofluorocarbons, such as 1,1-dichloro-1-fluoroethane (HCFC-141b) and dichlorotrifluorothane (HCFC-123 or HCFC-123a), will not adversely affect atmospheric chemistry, being negligible contributors to ozone depletion and to green-house global warming in comparison to the fully halogenated species. Both HCFC-141b and dichlorotrifluoroethane are known to be useful as solvents.

Commonly assigned U.S. Pat. No. 4,836,947 discloses azeotrope-like mixtures of 1,1-dichloro-1-fluoroethane and ethanol. Commonly assigned U.S. Pat. No. 4,842,764 discloses azeotrope-like mixtures of 1,1-dichloro-1-fluoroethane and methanol. Commonly assigned U.S. Pat. No. 4,863,630 discloses azeotrope-like mixtures of 1,1-dichloro-1-fluoroethane; dichlorotrifluoroethane; and ethanol. Commonly assigned U S. Pat. No. 4,894,176 discloses azeotrope-like mixtures of 1,1-dichloro-1-fluoroethane; dichlorotrifluoroethane; and methanol.

Kokai Patent Publication 103,686, published Apr. 20, 1989, discloses an azeotropic mixture of 55 to 80 weight percent dichlorotrifluoroethane and 20 to 45 weight percent 1,1-dichloro-1-fluoroethane. Kokai Patent Publication 136,981, published May 30, 1989, discloses a degreasing cleaning agent of an azeotropic mixture of 67 weight percent 1,1-dichloro-2,2,2-trifluoroethane and 33 weight percent 1,1-dichloro-1-fluoroethane, plus hydrocarbons, alcohols, ketones, chlorinated hydrocarbons, and esters.

Kokai Patent Publication 136,982, published May 30, 1989, discloses a buff-grinding cleaning agent of an azeotropic mixture of 67 weight percent 1,1-dichloro-2,2,2-trifluoroethane and 33 weight percent 1,1-dichloro-1-fluoroethane, plus hydrocarbons, alcohols, ketones, chlorinated hydrocarbons, and esters. Kokai Patent Publication 137,253, published May 30, 1989, discloses a resist developing agent of an azeotropic composition of 67 weight percent 1,1-dichloro-2,2,2-trifluoroethane and 33 weight percent 1,1-dichloro-1-fluoroethane, plus hydrocarbons, alcohols, ketones, chlorinated hydrocarbons, and esters.

Kokai Patent Publication 137,259, published May 30, 1989, discloses a resist separating agent of an azeotropic composition of 67 weight percent 1,1-dichloro-2,2,2-trifluoroethane and 33 weight percent 1,1-dichloro-1-fluoroethane, plus hydrocarbons, alcohols, ketones, chlorinated hydrocarbons, aromatics, and esters. Kokai Patent Publication 138,300, published May 31, 1989, discloses a flux cleaning agent of an azeotrope of 67 weight percent 1,1-dichloro-2,2,2-trifluoroethane and 33 weight percent 1,1-dichloro-1-fluoroethane, plus hydrocarbons, alcohols, ketones, and chlorinated hydrocarbons.

Kokai Patent Publication 139,104, published May 31, 1989, discloses a solvent of an azeotropic mixture of 67 weight percent 1,1-dichloro-2,2,2-trifluoroethane and 33 weight percent 1,1-dichloro-1-fluoroethane, plus hydrocarbons, alcohols, ketones, chlorinated hydrocarbons, and surfactants. Kokai Patent Publication 139,861, published June 1, 1989, discloses a dry-cleaning agent of 67 weight percent 1,1-dichloro-2,2,2-trifluoroethane and 33 weight percent 1,1-dichloro-1-fluoroethane, plus hydrocarbons, alcohols, ketones, chlorinated hydrocarbons, and surfactants.

It is an object of this invention to provide novel azeotrope-like compositions based on HCFC-141b and dichlorotrifluoroathane which are liquid at room temperature, which will not fractionate substantially under the process of distillation or evaporation, and which are useful as solvents for use in vapor degreasing and other solvent cleaning applications including defluxing applications and dry cleaning.

Another object of the invention is to provide novel environmentally acceptable solvents for use in the aforementioned applications.

Other objects and advantages of the invention will become apparent from the following description.

DESCRIPTION OF THE INVENTION

In accordance with the invention, novel mixtures have been discovered comprising 1,1-dichloro-1-fluoroethane; dichlorotrifluoroethane; methanol; and alkene having 5 carbon atoms. Also, novel azeotrope-like or constant-boiling compositions have been discovered comprising 1,1-dichloro-1-fluoroethane; dichlorotrifluoroethane; methanol; and alkene having 5 carbon atoms. The alkene having 5 carbon atoms is selected from the group consisting of 2-methyl-1-butene; 2-methyl-2-butene cyclopentene; 1-pentene: and 2-pentene. The dichlorotrifluoroethane component can be one of its isomers: 1,1-dichloro-2,2,2-trifluoroethane (HCFC-123); 1,2-dichloro-1,1,2-trifluoroethane (HCFC-123a); or mixtures thereof in any proportions.

The preferred isomer of dichlorotrifluoroethane is HCFC-123. Preferably, "commercial HCFC-123" which is available as "pure" HCFC-123 containing about 90 to about 95 weight percent of HCFC-123, about 5 to about 10 weight percent of HCFC-123a, and impurities such as trichloromonofluoromethane, trichlorotrifluoroethane, and methylene chloride which due to their presence in insignificant amounts, have no deleterious effects on the Properties of the azeotrope-like compositions, is used. "Commercial HCFC-123" is also available as "ultra-pure" HCFC-123 which contains about 95 to about 99.5 weight percent of HCFC-123, about 0.5 to about 5 weight percent of HCFC-123a, and impurities as listed above.

Preferably, the novel azeotrope-like compositions comprise effective amounts of 1,1-dichloro-1-fluoroethane; dichlorotrifluoroethane; methanol: and alkene having 5 carbon atoms. The term "effective amounts" as used herein means the amount of each component which upon combination with the other component, results in the formation of the present azeotrope-like composition.

Preferably, novel azeotrope-like compositions comprise 1,1-dichloro-1-fluoroethane; dichlorotrifluoroethane; methanol; and alkene having 5 carbon atoms selected from the group consisting of 2-methyl-1-butene; 2-methyl-2-butene; cyclopentene; 1-pentene;

and 2-Pentene which boil at about 30.0° C.±about 0.5° C. at 760 mm Hg (101 kPa).

Preferably, novel azeotrope-like compositions comprise from about 55 to about 97.8 weight percent of 1,1-dichloro-1-fluoroethane; from about 1 to about 38 weight percent of dichlorotrifluoroethane selected from the group consisting of 1,1-dichloro-2,2,2-trifluoroethane, 1,2-dichloro-1,1,2-trifluoroethane, or mixtures thereof; from about 1.0 to about 4.0 weight percent of methanol; and from about 0.2 to about 6.0 weight percent of alkene having 5 carbon atoms selected from the group consisting of 2-methyl-1-butane; 2-methyl-2-butene; cyclopentene; 1-pentene; and 2-Pentene which boil at about 30.0° C.±about 0.5° C. at 763 mm Hg (101 kPa).

When the dichlorotrifluoroethane used is 1,1-dichloro-2,2,2-trifluoroethane, novel azeotrope-like compositions preferably comprise 1,1-dichloro-1-fluoroethane; 1,1-dichloro-2,2,2-trifluoroethane; methanol; and 2-methyl-1-butene which boil at about 30.0° C.±about 0.5° C. at 760 mm Hg (101 kPa).

Novel azeotrope-like compositions also preferably Comprise from about 55 to about 97.8 weight percent of 1,1-dichloro-1-fluoroethane; from about 1 to about 38 weight percent of 1,1-dichloro-2,2,2-trifluoroethane; from about 1.0 to about 4.0 weight percent of methanol; and from about 0.2 to about 5.0 weight percent of 2-methyl-1-butene which boil at about 29.8° C. at 760 mm Hg (101 kPa).

Preferably the azeotrope-like compositions of the invention comprise from about 58.2 to about 95.0 weight percent of 1,1-dichloro-1-fluoroethane; from about 1 to about 35 weight percent of 1,1-dichloro-2,2,2-trifluoroethane; from about 2.0 to about 3.8 weight percent of methanol; and from about 2.0 to about 3.0 weight percent of 2-methyl-1-butene.

Most preferably, the azeotrope-like compositions of the invention comprise from about 60.2 to about 90.5 weight percent of 1,1-dichloro-1-fluoroethane; from about 5 to about 33 weight percent of 1,1-dichloro-2,2,2-trifluoroethane; from about 2.5 to about 3.8 weight percent of methanol; and from about 2.0 to about 3.0 weight percent of 2-methyl-1-butene.

Because the boiling point of 1,1-dichloro-2,2,2-trifluoroethane is 27.8° C. and the boiling point of 1,2-dichloro-1,1,2-trifluoroethane is 29.9° C., it is believed that azeotrope-like compositions of 1,2-dichloro-1,1,2-trifluoroethane; 1,1-dichloro-1-fluoroethane; methanol; and 2-methyl-1-butene would form. It should be understood that the aforementioned compositional ranges for azeotrope-like compositions of 1,1-dichloro-1-fluoroethane; 1,1-dichloro-2,2,2-trifluoroethane; methanol; and 2-methyl-1-butene also apply to azeotrope-like compositions of 1,1-dichloro-1-fluoroethane; 1,2-dichloro-1,1,2-trifluoroethane; methanol; and 2-methyl-1-butene.

Because the boiling point of 1,1-dichloro-2,2,2-trifluoroethane is so close to the boiling point of 1,2-dichloro-1,1,2-trifluoroethane, it is also believed that azeotrope-like compositions of 1,1-dichloro-1-fluoroethane; a mixture of 1,1-dichloro-2,2,2-trifluoroethane and 1,2-dichloro-1,1,2-trifluoroethane; methanol; and 2-methyl-1-butene would form. Preferably, azeotrope-like compositions comprise from about 55 to about 97.8 weight Percent of 1,1-dichloro-1-fluoroethane; from about 1 to about 38 weight percent of a mixture of 1,1-dichloro-2,2,2-trifluoroethane and 1,2-dichloro-1,1,2-trifluoroethane; from about 1.0 to about 4.0 weight percent of methanol; and from about 0.2 to about 5.0 weight percent of 2-methyl-1-butene.

More preferably, the azeotrope-like compositions of the invention comprise from about 58.2 to about 95.0 weight percent of 1,1-dichloro-1-fluoroethane; from about 1 to about 38 weight percent of a mixture of 1,1-dichloro-2,2,2-trifluoroethane and 1,2-dichloro-1,1,2-trifluoroethane; from about 2.0 to about 4.0 weight percent of methanol; and from about 2.0 to about 3.0 weight percent of 2-methyl-1-butene.

Most preferably, the azeotrope-like compositions of the invention comprise from about 60.2 to about 90.5 weight percent of 1,1-dichloro-1-fluoroethane; from about 5 to about 33 weight percent of a mixture of 1,1-dichloro-2,2,2-trifluoroethane and 1,2-dichloro-1,1,2-trifluoroethane; from about 2.5 to about 3.8 weight percent of methanol; and from about 2.0 to about 3.0 weight percent of 2-methyl-1-butene.

Also when the dichlorotrifluoroethane used is 1,1-dichloro-2,2,2-trifluoroethane, novel azeotrope-like compositions preferably comprise 1,1-dichloro-1-fluoroethane; 1,1-dichloro-2,2,2-trifluoroethane; methanol; and 2-methyl-2-butene which boil at about 29.9° C.±about 0.4° C. at 760 mm Hg (101 kPa).

Novel azeotrope-like compositions also preferably comprise from about 55 to about 97.8 weight percent of 1,1-dichloro-1-fluoroethane; from about 1 to about 38 weight percent of 1,1-dichloro-2,2,2-trifluoroethane; from about 1.0 to about 4.0 weight percent of methanol; and from about 0.2 to about 5.0 weight percent of 2-methyl-2-butene which boil at about 29.9° C. at 760 mm Hg (101 kPa).

Preferably the azeotrope-like compositions of the invention comprise from about 57 to about 94.0 weight percent of 1,1-dichloro-1-fluoroethane; from about 3 to about 35 weight percent of 1,1-dichloro-2,2,2-trifluoroethane; from about 2.0 to about 4.0 weight percent of methanol; and from about 1.0 to about 4.0 weight percent of 2-methyl-2-butene.

Most preferably, the azeotrope-like compositions of the invention comprise from about 60.2 to about 90.7 weight percent of 1,1-dichloro-1-fluoroethane; from about 5 to about 32 weight percent of 1,1-dichloro-2,2,2-trifluoroethane; from about 2.8 to about 3.9 weight percent of methanol; and from about 1.5 to about 3.9 weight percent of 2-methyl-2-butene.

Because the boiling point of 1,1-dichloro-2,2,2-trifluoroethane is 27.8° C. and the boiling point of 1,2-dichloro-1,1,2-trifluoroethane is 29.° C., it is believed that azeotrope-like compositions of 1,2-dichloro-1,1,2-trifluoroethane; 1,1-dichloro-1-fluoroethane; methanol; and 2-methyl-2-butene would form. It should be understood that the aforementioned compositional ranges for azeotrope-like compositions of 1,1-dichloro-1-fluoroethane; 1,1-dichloro-2,2,2-trifluoroethane; methanol; and 2-methyl-2-butene also apply to azeotrope-like compositions of 1.1-dichloro-1-fluoroethane; 1,2-dichloro-1,1,2-trifluoroethane; methanol; and 2-methyl-2-butene.

Because the boiling point of 1,1-dichloro-2,2,2-trifluoroethane is so close to the boiling point of 1,2-dichloro-1,1,2-trifluoroethane, it is also believed that azeotrope-like compositions of 1,1-dichloro-1-fluoroethane; a mixture of 1,1-dichloro-2,2,2-trifluoroethane and 1,2-dichloro-1,1,2-trifluoroethane; methanol; and 2-methyl-2-butene would form. Preferably, azeotrope-like compositions comprise from about 55 to about 97.8 weight percent of 1,1-dichloro-1-fluoroethane; from about 1 to about 38 weight percent of a mixture of 1,1-dichloro-2,2,2-trifluoroethane and 1,2-dichloro-1,1,2-trifluoroethane; from about 1.0 to about 4.0 weight percent of methanol; and from about 0.2 to about 5.0 weight percent of 2-methyl-2-butene.

More preferably, the azeotrope-like compositions of the invention comprise from about 57 to about 94.0 weight percent of 1,1-dichloro-1-fluoroethane; from about 3 to about 35 weight Percent of a mixture of 1,1-dichloro-2,2,2-trifluoroethane and 1,2-dichloro-1,1,2-trifluoroethane; from about 2.0 to about 4.0 weight percent methanol; and from about 1.0 to about 4.0 weight percent 2-methyl-2-butene.

Most preferably, the azeotrope-like compositions of the invention comprise from about 60.2 to about 90.7 weight percent of 1,1-dichloro-1-fluoroethane; from about 5 to about 32 weight percent of a mixture of 1,1-dichloro-2,2,2-trifluoroethane and 1,2-dichloro-1,1,2-trifluoroethane; from about 2.8 to about 3.9 weight percent methanol; and from about 1.5 to about 3.9 weight percent 2-methyl-2-butene.

Also when the dichlorotrifluoroethane used is 1,1-dichloro-2,2,2-trifluoroethane, novel azeotrope-like compositions preferably comprise 1,1-dichloro-1-fluoroethane; 1,1-dichloro-2,2,2-trifluoroethane; methanol; and cyclopentene which boil at about 30.1° C.±about 0.3° C. at 760 mm Hq (101 kPa).

Novel azeotrope-like compositions also preferably comprise from about 55 to about 97.5 weight percent of 1,1-dichloro-1-fluoroethane; from about 1 to about 37 weight percent of 1,1-dichloro-2,2,2-trifluoroethane; from about 1.0 to about 4.0 weight percent of methanol; and from about 0.5 to about 4.0 weight percent of cyclopentene which boil at about 30.1° C. at 760 mm Hg (101 kPa).

Preferably the azeotrope-like compositions of the invention comprise from about 57 to about 97.5 weight percent of 1,1-dichloro-1-fluoroethane; from about 1 to about 35 weight percent of 1,1-dichloro-2,2,2-trifluoroethane; from about 1.0 to about 4.0 weight Percent of methanol; and from about 0.5 to about 4.0 weight percent of cyclopentene.

Most preferably, the azeotrope-like compositions of the invention comprise from about 60 to about 95 weight Percent of 1,1-dichloro-1-fluoroethane; from about 1 to about 32 weight percent of 1,1-dichloro-2,2,2-trifluoroethane; from about 2.0 to about 4.0 weight percent of methanol; and from about 2.0 to about 4.0 weight percent of cyclopentene.

Because the boiling point of 1,1-dichloro-2,2,2-trifluoroethane is 27.8° C. and the boiling point of 1,2-dichloro-1,1,2-trifluoroethane is 29.9° C., it is believed that azeotrope-like compositions of 1,2-dichloro-1,1,2-trifluoroethane; 1,1-dichloro-1-fluoroethane; methanol; and cyclopentene would form. It should be understood that the aforementioned compositional ranges for azeotrope-like compositions of 1,1-dichloro-1-fluoroethane; 1,1-dichloro-2,2,2-trifluoroethane; methanol; and cyclopentene also apply to azeotrope-like compositions of 1,1-dichloro-1-fluoroethane; 1,2-dichloro-1,1,2-trifluoroethane; methanol; and cyclopentene.

Because the boiling point of 1,1-dichloro-2,2,2-trifluoroethane is so close to the boiling point of 1,2-dichloro-1,1,2-trifluoroethane, it is also believed that azeotrope-like compositions of 1,1-dichloro-1-fluoroethane; a mixture of 1,1-dichloro-2,2,2-trifluoroethane and 1,2-dichloro-1,1,2-trifluoroethane; methanol; and cyclopentene would form. Preferably, azeotrope-like compositions comprise from about 55 to about 97.5 weight percent of 1,1-dichloro-1-fluoroethane; from about 1 to about 37 weight percent of a mixture of 1,1-dichloro-2,2,2-trifluoroethane and 1,2-dichloro-1,1,2-trifluoroethane; from about 1.0 to about 4.0 weight percent of methanol; and from about 0.5 to about 4.0 weight percent of cyclopentene.

More preferably, the azeotrope-like compositions of the invention comprise from about 57 to about 97.5 weight percent of 1,1-dichloro-1-fluoroethane; from about 1 to about 35 weight percent of a mixture of 1,1-dichloro-2,2,2-trifluoroethane and 1,2-dichloro-1,1,2-trifluoroethane; from about 1.0 to about 4.0 weight percent o: methanol; and from about 0.5 to about 4.0 weight percent of cyclopentene.

Most preferably, the azeotrope-like compositions of the invention comprise from about 60 to about 95 weight percent of 1,1-dichloro-1-fluoroethane; from about 1 to about 32 weight percent of a mixture of 1,1-dichloro-2,2,2-trifluoroethane and 1,2-dichloro-1,1,2-trifluoroethane; from about 2.0 to about 4.0 weight percent of methanol; and from about 2.0 to about 4.0 weight percent of cyclopentene.

Also when the dichlorotrifluoroethane used is 1,1-dichloro-2,2,2-trifluoroethane, novel azeotrope-like compositions preferably comprise 1,1-dichloro-1-fluoroethane; 1,1-dichloro-2,2,2-trifluoroethane; methanol; and 1-pentene which b>il at about 30.3° C.±about 0.2° C. at 760 mm Hg (101 kPa).

Novel azeotrope-like compositions also preferably comprise from about 55 to about 97.8 weight percent of 1,1-dichloro-1-fluoroethane; from about 1 to about 38 weight percent of 1,1-dichloro-2,2,2-trifluoroethane; from about 1.0 to about 4.0 weight percent of methanol; and from about 0.2 to about 5.0 weight percent of 1-pentene which boil at about 30.3° C. at 760 mm Hg (101 kPa).

Preferably the azeotrope-like compositions of the invention comprise from about 57.2 to about 95.0 weight percent of 1,1-dichloro-1-fluoroethane; from about 1 to about 35 weight percent of 1,1-dichloro-2,2,2-trifluoroethane; from about 2.5 to about 3.8 weight percent of methanol; and from about 1.5 to about 4.0 weight percent of 1-pentene.

Most preferably, the azeotrope-like compositions of the invention comprise from about 60.9 to about 92.5 weight percent of 1,1-dichloro-1-fluoroethane; from about 3 to about 32 weight percent of 1,1-dichloro-2,2,2-trifluoroethane; from about 2.7 to about 3.1 weight Percent of methanol; and from about 1.8 to about 4.0 weight percent of 1-pentene.

Because the boiling point of 1,1-dichloro-2,2,2-trifluoroethane is 27.8° C. and the boiling point of 1,2-dichloro-1,1,2-trifluoroethane is 29.9° C., it is believed that azeotrope-like compositions of 1,2-dichloro-1,1,2-trifluoroethane; 1,1-dichloro-1-fluoroethane; methanol; and 1-pentene would form. It should be understood that the aforementioned compositional ranges for azeotrope-like compositions of 1,1-dichloro-1-fluoroethane; 1,1-dichloro-2,2,2-trifluoroethane; methanol; and 1-pentene also apply to azeotrope-like compositions of 1,1-dichloro-1-fluoroethane; 1,2-dichloro-1,1,2-trifluoroethane; methanol; and 1-pentene.

Because the boiling point of 1,1-dichloro-2,2,2-trifluoroethane is so close to the boiling point of 1,2-dichloro-1,1,2-trifluoroethane, it is also believed that azeotrope-like compositions of 1,1-dichloro-1-fluoroethane; a mixture of 1,1-dichloro-2,2,1-trifluoroethane and 1,2-dichloro-1,1,2-trifluoroethane; methanol; and 1-pentene would form. Preferably, azeotrope-like compositions comprise from about 55 to about 97.8 weight percent of 1,1-dichloro-1-fluoroethane; from about 1 to about 38 weight percent of a mixture of 1,1-dichloro-2,2,2-trifluoroethane and 1,2-dichloro-1,1,2-trifluoroethane; from about 1.0 to about 4.0 weight percent of methanol; and from about 0.2 to about 5.0 weight percent of 1-pentene.

More preferably, the azeotrope-like compositions of the invention comprise from about 57.2 to about 95.0 weight percent of 1,1-dichloro-1-fluoroethane; from about to about 35 weight percent of a mixture of 1,1-dichloro-2,2,2-trifluoroethane and 1,2-dichloro-1,1,2-trifluoroethane; from about 2.5 to about 3.8 weight percent of methanol; and from about 1.5 to about 4.0 weight percent of 1-pentene.

Most preferably, the azeotrope-like compositions of the invention comprise from about 60.9 to about 92.5 weight percent of 1,1,2-dichloro-1-fluoroethane; from about to about 32 weight percent of a mixture of 1,1-dichloro-2,2,2-trifluoroethane and 1,2-dichloro-1,1,2-trifluoroethane; from about 2.7 to about 3.1 weight percent of methanol; and from about 1.8 to about 4.0 weight percent of 1-pentene.

Also when the dichlorotrifluoroethane used is 1,1-dichloro-2,2,2-trifluoroethane, novel azeotrope-like compositions preferably comprise 1,1-dichloro-1-fluoroethane; 1,1-dichloro-2,2,2-trifluoroethane; methanol; and 2-pentene which boil at about 29.8° C.±about 0.3° C. at 760 mm Hg (101 kPa).

Novel azeotrope-like compositions also preferably comprise from about 55 to about 97.8 weight percent of 1,1-dichloro-1-fluoroethane; from about 1 to about 38 weight percent of 1,1-dichloro-2,2,2-trifluoroethane; from about 1.0 to about 4.0 weight percent of methanol; and from about 0.2 to about 6.0 weight percent of 2-pentene which boil at about 29.8° C. at 760 mm Hg (101 kPa).

Preferably the azeotrope-like compositions of the invention comprise from about 55.2 to about 93.0 weight percent of 1,1-dichloro-1-fluoroethane; from about 3 to about 35 weight percent of 1,1-dichloro-2,2,2-trifluoroethane; from about 2.0 to about 3.8 weight percent of methanol; and from about 2.0 to about 6.0 weight percent of 2-pentene.

Most preferably, the azeotrope-like compositions of the invention comprise from about 58.7 to about 90.7 weight percent of 1,1-dichloro-1-fluoroethane; from about 5 to about 32 weight percent of 1,1-dichloro-2,2,2-trifluoroethane; from about 2.0 to about 3.5 weight percent of methanol; and from about 2.3 to about 5.8 weight percent of 2-pentene.

Because the boiling point of 1,1-dichloro-2,2,2-trifluoroethane is 27.8° C. and the boiling point of 1,2-dichloro-1,1,2-trifluoroethane is 29.9° C., it is believed that azeotrope-like compositions of 1,2-dichloro-1,1,2-trifluoroethane; 1,1-dichloro-1-fluoroethane; methanol; and 2-pentene would form. It should be understood that the aforementioned compositional ranges for azeotrope-like compositions of 1,1-dichloro-1-fluoroethane; 1,1-dichloro-2,2,2-trifluoroethane; methanol; and 2-pentene also apply to azeotrope-like compositions of 1,1-dichloro-1-fluoroethane; 1,2-dichloro-1,1,2-trifluoroethane; methanol; and 2-pentene.

Because the boiling point of 1,1-dichloro-2,2,2-trifluoroethane is so close to the boiling point of 1,2-dichloro-1,1,2-trifluoroethane, it is also believed that azeotrope-like compositions of 1,1-dichloro-1-fluoroethane; a mixture of 1,1-dichloro-2,2,2-trifluoroethane and 1,2-dichloro-1,1,2-trifluoroethane; methanol; and 2-pentene would form. Preferably, azeotrope-like compositions comprise from about 55 to about 97.8 weight percent of 1,1-dichloro-1-fluoroethane; from about 1 to about 38 weight percent of a mixture of 1,1-dichloro-2,2,2-trifluoroethane and 1,2-dichloro-1,1,2-trifluoroethane; from about 1.0 to about 4.0 weight percent of methanol; and from about 0.2 to about 6.0 weight percent of 2-pentene.

More preferably, the azeotrope-like compositions of the invention comprise from about 55.2 to about 93.0 weight percent of 1,1-dichloro-1-fluoroethane; from about 3 to about 35 weight percent of a mixture of 1,1-dichloro-2,2,2-trifluoroethane and 1,2-dichloro-1,1,2-trifluoroethane; from about 2.0 to about 3.8 weight percent of methanol; and from about 2.0 to about 6.0 weight percent of 2-pentene.

Most preferably, the azeotrope-like compositions of the invention comprise from about 58.7 to about 90.7 weight percent of 1,1-dichloro-1-fluoroethane; from about 5 to about 32 weight percent of a mixture of 1,1-dichloro-2,2,2-trifluoroethane and 1,2-dichloro-1,1,2-trifluoroethane; from about 2.0 to about 3.5 weight percent of methanol; and from about 2.3 to about 5.8 weight percent of 2-pentene.

As previously noted, the preferred dichlorotrifluoroethane component is "commercial HCFC-123".

The azeotrope-like compositions of the invention containing a mixture of HCFC-123 and HCFC-123a are azeotrope-like in that they are constant-boiling or essentially constant-boiling. It is not known whether this is the case because the separate ternary azeotrope-like compositions with HCFC-123 and HCFC-123a have boiling points so close to one another as to be indistinguishable for practical purposes or whether HCFC-123 and HCFC-123a form a quaternary azeotrope with 1,1-dichloro-1-fluoroethane and 2-methyl-1-butene; 2-methyl-2-butene; cyclopentene; 1-pentene; or 2-pentene.

All compositions within the indicated ranges, as well as certain compositions outside the indicated ranges, are azeotrope-like, as defined more particularly below.

The 1,1-dichloro-1-fluoroethane and dichlorotrifluoroethane components of the invention have good solvent properties. The methanol and alkene components also have good solvent capabilities. Thus, when these components are combined in effective amounts, an efficient azeotrope-like solvent results.

The precise azeotrope compositions have not been determined but have been ascertained to be within the above ranges. Regardless of where the true azeotropes lie, all compositions with the indicated ranges, as well as certain compositions outside the indicated ranges, are azeotrope-like, as defined more particularly below.

It has been found that these azeotrope-like compositions are on the whole nonflammable liquids. i.e. exhibit no flash point when tested by the Tag Open Cup test method—ASTM D 1310-86.

From fundamental principles, the thermodynamic state of a fluid is defined by four variables: pressure, temperature, liquid composition and vapor composition, or P-T-X-Y, respectively. An azeotrope is a unique characteristic of a system of two or more components where X and Y are equal at the stated P and T. In practice, this means that the components of a mixture cannot be separated during distillation, and therefore are useful in vapor phase solvent cleaning as described above.

For the purpose of this discussion, azeotrope-like composition is intended to mean that the composition behaves like an azeotrope, i.e. has constant-boiling characteristics or a tendency not to fractionate upon boiling or evaporation. Thus, in such compositions, the composition of the vapor formed during boiling or evaporation is identical or substantially identical to the original liquid composition. Hence, during boiling or evaporation, the liquid composition, if it changes at all, changes only to a minimal or negligible extent. This is to be contrasted with non-azeotrope-like compositions in which during boiling or evaporation, the liquid composition changes to a substantial degree.

Thus, one way to determine whether a candidate mixture is "azeotrope-like" within the meaning of this invention, is to distill a sample thereof under conditions (i.e. resolution number of plates) which would be expected to separate the mixture into its separate components. If the mixture is non-azeotrope-like, the mixture will fractionate, i.e. separate into its various components with the lowest boiling component distilling off first, and so on. If the mixture is azeotrope-like, some finite amount of a first distillation cut will be obtained which contains all of the mixture components and which is constant-boiling or behaves as a single substance. This phenomenon cannot occur if the mixture is not azeotrope-like, i.e. it does not behave like an azeotrope. Of course, upon distillation of an azeotrope-like composition such as in a vapor degreaser, the true azeotrope will form and tend to concentrate.

It follows from the above that another characteristic of azeotrope-like compositions is that there is a range of compositions containing the same components in varying proportions which are azeotrope-like or constant-boiling. All such compositions are intended to be covered by the term azeotrope-like or constant-boiling as used herein. As an example, it is well known that at differing pressures, the composition of a given azeotrope-like composition will vary at least slightly as does the boiling point of the composition. Thus, an azeotrope-like composition of A and B represents a unique type of relationship but with a variable composition depending on temperature and/or pressure.

With 1,1-dichloro-1-fluoroethane; 1,1-dichloro-2,2,2-trifluoroethane; methanol; and 2-methyl-1-butene, the mixtures boil within ±about 0.5° C. (at about 760 mm Hg (101 kPa)) of the 30.0° C. boiling point. With 1,1-dichloro-1-fluoroethane; 1,1-dichloro-2,2,2-trifluoroethane; methanol; and 2-methyl-2-butene, the mixtures boil within ±about 0.4° C. (at about 760 mm Hg (101 kPa)) of the 29.9° C. boiling point. With 1,1-dichloro-1-fluoroethane; 1,1-dichloro-2,2,2-trifluoroethane; methanol; and cyclopentene, the mixtures boil within ±about 0.3° C. (at about 760 mm Hg (101 kPa)) of the 30.1° C. boiling point. With 1,1-dichloro-1-fluoroethane; 1,1-dichloro-2,2,2-trifluoroethane; methanol; and 1-pentene, the mixtures boil within ±about 0.2° C. (at about 760 mm Hg (101 kPa)) of the 30.3° C. boiling point. With 1,1-dichloro-1-fluoroethane; 1,1-dichloro-2,2,2-trifluoroethane; methanol; and 2-pentene, the mixtures boil within ±about 0.3° C. (at about 760 mm Hg (101 kPa)) of the 29.8° C. boiling point.

As is readily understood by persons skilled in the art, the boiling point of the azeotrope-like composition will vary with the pressure.

The azeotrope-like compositions of the invention are useful as solvents in a variety of vapor degreasing, cold cleaning and solvent cleaning applications including defluxing and dry cleaning and as blowing agents.

In one process embodiment of the invention, the azeotrope-like compositions of the invention may be used to clean solid surfaces by treating said surfaces with said compositions in any manner well known to the art such as by dipping or spraying or use of conventional degreasing apparatus.

The 1,1-dichloro-1-fluoroethane; dichlorotrifluoroethane; methanol; 2-methyl-1-butene; 2-methyl-2-butene; cyclopentene; 1-pentene; and 2-pentene components of the novel solvent azeotrope-like compositions of the invention are known materials and are commercially available. Preferably, except for "commercial HCFC-123" and its impurities, the materials should be used in sufficiently high purity so as to avoid the introduction of adverse influences upon the desired properties or constant boiling properties of the system. Commercially available cis-2-pentene; trans-2-pentene; or a mixture of the isomers is useful in the present invention.

It should be understood that the present compositions may include additional components so as to form new azeotrope-like or constant-boiling compositions. Any such compositions are considered to be within the scope of the present invention as long as the compositions are constant-boiling or essentially constant-boiling and contain all of the essential components described herein.

The present invention is more fully illustrated by the following non-limiting Examples.

EXAMPLE 1

This example confirms the existence of constant-boiling or azeotrope-like compositions of 1,1-dichloro-1-fluoroethane; 1,1-dichloro-2,2,2-trifluoroethane; methanol; and 2-methyl-1-butene via the method of distillation. It also illustrates that this mixture does not fractionate during distillation.

A 5-plate Oldershaw distillation column with a cold water condensed automatic liquid dividing head was used for this example. The distillation column was charged with HCFC-141b, commercially available ultra-pure HCFC-123, methanol, and 2-methyl-1-butene in the amounts indicated in Table I below for the starting material. The composition was heated under total reflux for about an hour to ensure equilibration. A reflux ratio of 2:1 was employed for this particular distillation. Approximately 50 percent of the original charges were collected in four similar-sized overhead fractions. The compositions of these fractions were analyzed using gas chromatography. The averages of the distillate fractions and the overhead temperatures are quite constant within the uncertainty associated with determining the compositions, indicating that the mixture is constant-boiling or azeotrope-like.

TABLE I

| Example | HCFC-141b | HCFC-123 | METHANOL | 2-METHYL-1-BUTENE |
|---|---|---|---|---|
| | | Starting Material (wt. %) | | |
| 1 | 84.78 | 9.82 | 3.40 | 2.00 |
| | | Distillate Compositions (wt. %) | | |
| 1 | 84.26 | 9.50 | 3.24 | 3.00 |

| Example | Boiling Point (°C.) | Barometric Pressure (mmHg) (kPa) | Boiling Point Corrected to 760 mmHg (101 kPa) |
|---|---|---|---|
| 1 | 29.3 | 748.8 (100) | 29.8 |

From the above example, it is readily apparent that additional constant-boiling or essentially constant-boiling mixtures of the same components can readily be identified by anyone of ordinary skill in this art by the method described. No attempt was made to fully characterize and define the outer limits of the composition ranges which are constant-boiling. Anyone skilled in the art can readily ascertain other constant-boiling or essentially constant-boiling mixtures containing the same components.

EXAMPLE 2

Example 1 is repeated except that 1,2-dichloro-1,1,2-trifluoroethane is used instead of 1,1-dichloro-2,2,2-trifluoroethane.

EXAMPLES 3-6

These examples confirm the existence of constant-boiling or azeotrope-like compositions of 1,1-dichloro-1-fluoroethane; 1,1-dichloro-2,2,2-trifluoroethane; methanol; and 2-methyl-2-butene via the method of distillation. It also illustrates that these mixtures do not fractionate during distillation.

A 5-plate Oldershaw distillation column with a cold water condensed automatic liquid dividing head was used for these examples. For each Example, the distillation column was charged with HCFC-141b, commercially available ultra-pure HCFC-123, methanol, and 2-methyl-2-butene in the amounts indicated in Table II below for the starting material. Each composition was heated under total reflux for about an hour to ensure equilibration. A reflux ratio of 5:1 was employed for this particular distillation. Approximately 50 percent of the original charges were collected in four similar-sized overhead fractions. The compositions of these fractions were analyzed using gas chromatography. The averages of the distillate fractions and the overhead temperatures are quite constant within the uncertainty associated with determining the compositions, indicating that the mixtures are constant-boiling or azeotrope-like.

TABLE II

| EX | HCFC-141b | HCFC-123 | METHANOL | 2-METHYL-2-BUTENE |
|---|---|---|---|---|
| | | Starting Material (wt. %) | | |
| 3 | 64.88 | 30.07 | 3.02 | 2.03 |
| 4 | 82.56 | 10.26 | 3.04 | 4.15 |
| 5 | 89.87 | 5.04 | 3.60 | 1.49 |
| 6 | 60.92 | 32.05 | 3.01 | 4.02 |
| | | Distillate Compositions (wt. %) | | |
| 3 | 62.71 | 32.21 | 2.98 | 2.10 |
| 4 | 82.46 | 10.12 | 3.54 | 3.88 |
| 5 | 89.85 | 4.80 | 3.82 | 1.53 |
| 6 | 60.27 | 33.05 | 2.84 | 3.84 |

| Example | Boiling Point (°C.) | Barometric Pressure (mmHg) (kPa) | Boiling Point Corrected to 760 mmHg (101 kPa) |
|---|---|---|---|
| 3 | 29.0 | 744.8 (99) | 29.6 |
| 4 | 29.5 | 744.8 (99) | 30.1 |
| 5 | 29.3 | 737.5 (98) | 30.2 |
| 6 | 29.1 | 747.4 (99) | 29.6 |
| | | | Mean 29.9° C. ± 0.3° C. |

From the above examples, it is readily apparent that additional constant-boiling or essentially constant-boiling mixtures of the same components can readily be identified by anyone of ordinary skill in this art by the method described. No attempt was made to fully characterize can define the outer limits of the composition ranges which are constant-boiling. Anyone skilled in the art can readily ascertain other constant-boiling or essentially constant-boiling mixtures containing the same components.

EXAMPLES 7-10

Examples 3 through 6 are repeated except that 1,2-dichloro-1,1,2-trifluoroethane is used instead of 1,1-dichloro-2,2,2-trifluoroethane.

EXAMPLES 11-12

These examples confirm the existence of constant-boiling or azeotrope-like compositions of 1,1-dichloro-1-fluoroethane; 1,1-dichloro-2,2,2-trifluoroethane; methanol; and cyclopentene via the method of distillation. It also illustrates that these mixtures do not fractionate during distillation.

A 5-plate Oldershaw distillation column with a cold water condensed automatic liquid dividing head was used for these examples. For each Example, the distillation column was charged with HCFC-141b, commercially available ultra-pure HCFC-123, methanol, and cyclopentene in the amounts indicated in Table III below for the starting material. Each composition was heated under total reflux for about an hour to ensure equilibration. A reflux ratio of 2:1 was employed for this particular distillation. Approximately 50 percent of the original charges were collected in four similar-sized overhead fractions. The compositions of these fractions were analyzed using gas chromatography. The averages of the distillate fractions and the overhead temperatures are quite constant within the uncertainty associated with determining the compositions. indicating that the mixtures are constant-boiling or azeotrope-like.

TABLE III

| Example | HCFC-141b | HCFC-123 | METHANOL | CYCLOPENTENE |
|---|---|---|---|---|
| | | Starting Material (wt. %) | | |
| 11 | 87.88 | 5.02 | 3.07 | 4.03 |
| 12 | 62.82 | 30.21 | 2.99 | 3.98 |
| | | Distillate Compositions (wt. %) | | |
| 11 | 87.41 | 5.15 | 4.09 | 3.35 |
| 12 | 62.35 | 31.54 | 2.95 | 3.16 |

| Example | Boiling Point (°C.) | Barometric Pressure (mmHg) (kPa) | Boiling Point Corrected to 760 mmHg (101 kPa) |
|---|---|---|---|
| 11 | 29.3 | 747.6 (99) | 29.8 |
| 12 | 29.9 | 747.6 (99) | 30.4 |
| | | | Mean 30.1° C. ± 0.3° C. |

From the above examples, it is readily apparent that additional constant-boiling or essentially constant-boiling mixtures of the same components can readily be identified by anyone of ordinary skill in this art by the method described. No attempt was made to fully characterize and define the outer limits of the composition ranges which are constant-boiling. Anyone skilled in the art can readily ascertain other constant-boiling or essentially constant-boiling mixtures containing the same components.

EXAMPLES 13-14

Examples 11 and 12 are repeated except that 1,2-dichloro-1,1,2-trifluoroethane is used instead of 1,1-dichloro-2,2,2-trifluoroethane.

EXAMPLE 15

This example confirms the existence of constant-boiling or azeotrope-like compositions of 1,1-dichloro-1-fluoroethane; 1,1-dichloro-2,2,2-trifluoroethane; methanol; and 1-pentene via the method of distillation. It also illustrates that this mixture does not fractionate during distillation.

A 5-plate Oldershaw distillation column with a cold water condensed automatic liquid dividing head was used. The distillation column was charged with HCFC-141b, commercially available ultra-pure HCFC-123, methanol, and 1-pentene in the amounts indicated in Table IV below for the starting material. The composition was heated under total reflux for about an hour to ensure equilibration. A reflux ratio of 3:1 was employed for this particular distillation. Approximately 50 percent of the original charges were collected in four similar-sized overhead fractions. The compositions of these fractions were analyzed using gas chromatography. The averages of the distillate fractions and the overhead temperatures are quite constant within the uncertainty associated with determining the compositions, indicating that the mixture is constant-boiling or azeotrope-like.

TABLE IV

| Example | HCFC-141b | HCFC-123 | METHANOL | 1-PENTENE |
|---|---|---|---|---|
| | | Starting Material (wt. %) | | |
| 15 | 84.97 | 9.96 | 3.13 | 1.94 |
| | | Distillate Compositions (wt. %) | | |
| 15 | 84.01 | 9.61 | 2.68 | 3.70 |

| Example | Boiling Point (°C.) | Barometric Pressure (mmHg) (kPa) | Boiling Point Corrected to 760 mmHg (101 kPa) |
|---|---|---|---|
| 15 | 29.6 | 742.7 (99) | 30.3 |

From the above example, it is readily apparent that additional constant-boiling or essentially constant-boiling mixtures of the same components can readily be identified by anyone of ordinary skill in this art by the method described. No attempt was made to fully characterize and define the outer limits of the composition ranges which are constant-boiling. Anyone skilled in the art can readily ascertain other constant-boiling or essentially constant-boiling mixtures containing the same components.

EXAMPLE 16

Example 15 is repeated except that 1,2-dichloro-1,1,2-trifluoroethane is used instead of 1,1-dichloro-2,2,2-trifluoroethane.

EXAMPLES 17-19

These examples confirm the existence of constant-boiling or azeotrope-like compositions of 1,1-dichloro-1-fluoroethane; 1,1-dichloro-2,2,2-trifluoroethane; methanol; and 2-pentene via the method of distillation. It also illustrates that these mixtures do not fractionate during distillation.

A 5-plate Oldershaw distillation column with a cold water condensed automatic liquid dividing head was used for these examples. For each Example, the distillation column was charged with HCFC-141b, commercially available ultra-pure HCFC-123, methanol, and 2-pentene in the amounts indicated in Table V below for the starting material. Each composition was heated under total reflux for about an hour to ensure equilibration. A reflux ratio of 3:1 was employed for this particular distillation. Approximately 50 percent of the original charges were collected in four similar-sized overhead fractions. The compositions of these fractions were analyzed using gas chromatography. The averages of the distillate fractions and the overhead temperatures are quite constant within the uncertainty associated with determining the compositions, indicating that the mixtures are constant-boiling or azeotrope-like.

TABLE V

| Example | HCFC-141b | HCFC-123 | METHANOL | 2-PENTENE (CIS/TRANS) |
|---|---|---|---|---|
| | | Starting Material (wt. %) | | |
| 17 | 84.39 | 10.38 | 3.11 | 2.12 (0.59/1.53) |
| 18 | 64.93 | 30.14 | 2.96 | 1.97 (0.56/1.41) |
| 19 | 82.37 | 9.80 | 2.93 | 4.90 (2.00/2.90) |
| | | Distillate Compositions (wt. %) | | |
| 17 | 83.68 | 10.66 | 2.78 | 2.88 (0.74/2.14) |
| 18 | 63.47 | 31.15 | 3.01 | 2.37 (0.63/1.74) |
| 19 | 80.94 | 9.88 | 3.47 | 5.71 (2.21/3.50) |

| Example | Boiling Point (°C.) | Barometric Pressure (mmHg) (kPa) | Boiling Point Corrected to 760 mmHg (101 kPa) |
|---|---|---|---|
| 17 | 29.1 | 742.7 (99) | 29.8 |
| 18 | 29.3 | 747.3 (99) | 29.8 |
| 19 | 29.2 | 747.3 (99) | 29.7 |
| | | | Mean 29.8° C. ± 0.1° C. |

From the above examples, it is readily apparent that additional constant-boiling or essentially constant-boiling mixtures of the same components can readily be identified by anyone of ordinary skill in this art by the method described. No attempt was made to fully characterize and define the outer limits of the composition range which are constant-boiling. Anyone skilled in the art can readily ascertain other constant-boiling or essentially constant-boiling mixtures containing the same components.

EXAMPLES 20-22

Examples 17 through 19 are repeated except that 1,2-dichloro-1,1,2-trifluoroethane is used instead of 1,1-dichloro-2,2,2-trifluoroethane.

EXAMPLES 23-44

Performance studies are conducted wherein metal coupons are cleaned using the present azeotrope-like compositions as solvents. The metal coupons are soiled with various types of oils and heated to 93° C. so as to partially simulate the temperature attained while machining and grinding in the presence of these oils.

The metal coupons thus treated are degreased in a three-sump vapor phase degreaser machine. In this typical three-sump degreaser, condenser coils around the lip of the machine are used to condense the solvent vapor which is then collected in a sump. The condensate overflows into cascading sumps and eventually goes into the boiling sump.

The metal coupons are held in the solvent vapor and then vapor rinsed for a period of 15 seconds to 2 minutes depending upon the oils selected. The azeotrope-like compositions of Examples 1 through 22 are used as the solvents. Cleanliness testing of coupons are done by measurement of the weight change of the coupons using an analytical balance to determine the total residual materials left after cleaning.

Inhibitors may be added to the present azeotrope-like compositions to inhibit decomposition of the compositions; react with undesirable decomposition products of the compositions; and/or prevent corrosion of metal surfaces. Any or all of the following classes of inhibitors may be employed in the invention: epoxy Compounds such as propylene oxide; nitroalkanes such as nitromethane; ethers such as 1-4-dioxane; unsaturated compounds such as 1,4-butyne diol; acetals or ketals such as dipropoxy methane; ketones such as methyl ethyl ketone; alcohols such as tertiary amyl alcohol; esters such as triphenyl phosphite; and amines such as triethyl amine. Other suitable inhibitors will readily occur to those skilled in the art.

Having described the invention in detail and by reference to preferred embodiments thereof, it will be apparent that modifications and variations are possible without departing from the scope of the invention defined in the appended claims.

What is claimed is:

1. Azeotrope-like compositions consisting essentially of from about 55 to about 97.8 weight percent of 1,1-dichloro-1-fluoroethane, from about 1 to about 38 weight percent of dichlorotrifluoroethane selected from the group consisting of 1,1-dichloro-2,2,2-trifluoroethane and a mixture consisting of about 90 to about 99.5 weight percent of 1,1-dichloro-2,2,2-trifluoroethane and about 0.5 to about 10 weight percent 1,2-dichloro-1,1,2-trifluoroethane, from about 1.1 to about 4.0 percent by weight of methanol, and from about 0.2 to about 6.0 weight percent of cyclopentene which boil at about 30.0° C.±0.5° C. at 760 mm Hg.

2. The azeotrope-like compositions of claim 1 wherein said azeotrope-like compositions boil at about 30.1° C.±0.3° at 760 mm Hg.

3. The azeotrope-like compositions of claim 2 consisting essentially of from about 57 to about 97.5 weight percent said 1,1-dichloro-1-fluoroethane, from about 1 to about 35 weight percent said 1,1-dichloro-2,2,2-trifluoroethane, from about 1.1 to about 4.0 weight percent said methanol, and from about 0.5 to about 4.0 weight percent said cyclopentene.

4. The azeotrope-like compositions of claim 2 consisting essentially of from about 60 to about 95 weight percent said 1,1-dichloro-1-fluoroethane, from about 1 to about 32 weight percent said 1,1-dichloro-2,2,2-trifluoroethane, from about 2.0 to about 4.0 weight percent methanol, and from about 2.0 to about 4.0 weight percent said cyclopentene.

5. A method of cleaning a solid surface which comprises treating said surface with said azeotrope-like composition as defined in claim 2.

6. The azeotrope-like compositions of claim 1 wherein said dichlorotrifluoroethane is said mixture.

7. The azeotrope-like compositions of claim 1 consisting essentially of from about 57 to about 97.5 weight percent said 1,1-dichloro-1-fluoroethane, from about 1 to about 32 weight percent said mixture, from about 2.0 to about 4.0 weight percent said methanol, and from about 2.0 to about 4.0 weight percent said cyclopentene.

8. The azeotrope-like compositions of claim 1 consisting essentially of from about 60 to about 95 weight percent said 1,1-dichloro-1-fluoroethane, from about 1 to about 32 weight percent said mixture, from about 2.0 to about 4.0 weight percent said methanol, and from about 2.0 to about 4.0 weight percent said cyclopentene.

9. A method of cleaning a solid surface which comprises treating said surface with said azeotrope-like composition as defined in claim 6.

* * * * *